United States Patent [19]

Barth et al.

[11] Patent Number: 5,413,567
[45] Date of Patent: May 9, 1995

[54] PRIMARY PACKAGING FOR SURFACE-STABILIZED SURGICAL DRESSING

[75] Inventors: Peter Barth; Hans-Rainer Hoffmann; Walter Müller, all of Neuwied; Heinrich Kindel, Rengsdorf, all of Germany

[73] Assignee: LTS Lohmann Therapie-Systeme GmbH & Co. KG, Neuwied, Germany

[21] Appl. No.: 831,081

[22] Filed: Feb. 5, 1992

Related U.S. Application Data

[63] Continuation of Ser. No. 684,452, Apr. 11, 1991, abandoned, which is a continuation of Ser. No. 442,324, Nov. 24, 1989, abandoned.

[30] Foreign Application Priority Data

Feb. 29, 1988 [DE] Germany .................. 38 06 444.8

[51] Int. Cl.⁶ ............................................ A61F 13/02
[52] U.S. Cl. ........................................ 604/307; 206/440; 602/42; 602/58
[58] Field of Search ............ 206/440, 441; 604/890.1, 307, 305; 602/42, 58

[56] References Cited

U.S. PATENT DOCUMENTS

| | | | |
|---|---|---|---|
| 2,897,961 | 8/1959 | Bush | 206/441 |
| 3,072,249 | 1/1963 | Tritsch | 206/441 |
| 3,277,891 | 10/1966 | Hoey | 128/156 |
| 3,612,265 | 10/1971 | Dickerson | 206/441 |
| 4,450,844 | 5/1984 | Quisno | 128/743 |
| 4,542,013 | 9/1985 | Keith | . |
| 4,619,253 | 10/1986 | Anhäuser et al. | 128/156 |
| 4,695,277 | 9/1987 | Lauk | 128/156 |
| 4,706,662 | 11/1987 | Thompson | 602/44 |
| 4,742,826 | 5/1988 | McLorg | 206/440 |
| 4,765,478 | 8/1988 | Bringloe | 206/440 |
| 4,781,293 | 11/1988 | Johns | 206/441 |
| 4,787,380 | 11/1988 | Scott | 206/441 |
| 4,808,172 | 2/1989 | Murata | . |
| 4,915,102 | 4/1990 | Kwiatek et al. | . |
| 4,915,228 | 4/1990 | Johns | 206/441 |
| 5,099,832 | 3/1992 | Ward | 206/441 |

FOREIGN PATENT DOCUMENTS 1935916 2/1971 Germany .
3721595 1/1988 Germany .

*Primary Examiner*—Randall L. Green
*Assistant Examiner*—Rob Clarke
*Attorney, Agent, or Firm*—Kalish & Gilster

[57] ABSTRACT

The invention relates to a primary pack for surface-stabilized bandaging materials having a carrier layer and a skin-side contact surface having pressure sensitive adhesive areas and which prior to the use of the bandaging material is protected by a removable covering layer, and an at least one-layer supporting film detachably applied to the skin-remote surface of the carrier layer and which can be removed from the applied bandaging material, the supporting film forming part of the pack protecting the bandaging material.

16 Claims, 1 Drawing Sheet

PRIMARY PACKAGING FOR SURFACE-STABILIZED SURGICAL DRESSING

This application is a continuation of application Ser. No. 07/684,452, filed Apr. 11, 1991, now abandoned, which application is a continuation of application Ser. No. 07/442,324 filed Nov. 24, 1989, now abandoned.

BACKGROUND AND SUMMARY OF THE INVENTION

The invention relates to the primary pack of surface-stabilized bandaging materials, which have a carrier layer and a skin-side pressure sensitive surface having contact adhesive areas, which is protected prior to the use of the bandaging material by a removable covering layer and containing an at least one-layer supporting or backing film detachably applied to the carrier layer surface remote from the skin and which is removable from the applied bandaging material after fulfilling its function of surface stabilizing the carrier layer.

Bandaging materials can be subdivided into two major groups. The first group consists of those which are fixed at the point of their application by additional devices or measures, whereas the other group involves the fixing by pressure sensitive adhesive areas of the actual bandaging material. In the case of the latter group, the requirement for thin and flexible carrier layers ensuring a usable moisture penetration and good close adaptability to the contours of the application point led to difficulties during application. Thus, after removing the covering layer, there can e.g. be rolling in of the marginal regions, the sticking together of pressure sensitive adhesive areas and creasing, which makes the bandaging material unusable.

An improvement is attainable by using a so-called supporting or backing film for surface stabilization purposes, a more rigid layer than the carrier layer being so connected thereto that it can be detached following application (DE-OS 19 35 916). This principle has proven satisfactory in practice (cf. German patent 33 44 334, U.S. Pat. No. 4,619,253).

However, it must be looked upon as disadvantageous that the supporting film is thrown away after removal from the applied bandaging material and consequently its function is limited to surface stabilization. The expenditure involved in providing the material and the manufacturing measures for this additional element of such bandaging materials is not inconsiderable.

The problem of the invention is therefore to so extend the function, of the supporting film that the cost/use ratio becomes more favorable.

The problem of the invention is solved by a primary pack of the aforementioned type in which the supporting film is part of the pack protecting the bandaging material. In the sense of the invention, the term primary packaging is understood to mean a protective layer directly enveloping the bandaging material. The thus packed individual pieces can be combined to larger units by secondary and tertiary packs. The actual protection of the substrate is mainly ensured by the primary pack. Advantageous further developments can be gathered from the claims.

The invention is usable in all bandaging materials surface-stabilized by supporting films. These bandaging materials are known and are e.g. used as wound bandages, fixing bandages, active substance-delivering plaster and incision films or foils. The carrier layer of the bandaging material can e.g. be a textile material, a polymer material or a metal-containing layer. The supporting film is constituted by an at least one-layer flat structure of materials containing polymers, paper or metal. Its surface has at least the same extension as the carrier layer, but according to a preferred embodiment of the invention can project on one or more sides over the carrier layer edge. The detachable connection between the supporting film and the carrier layer can be produced by known methods, such as e.g. producing the carrier layer directly on the supporting film, heat sealing, welding, adhesion, bonding, embossing or forming electrostatic attraction forces.

The materials for producing the pressure sensitive adhesive areas ensuring contact with the skin are selected from the vast number of possibilities under the standpoint of physiological non-objectionability. A removable covering layer protects the skin contact surface of the bandaging material prior to use.

The sense and purpose of a primary pack for such a bandaging material are known to the expert. The hitherto known solution of introducing the bandaging material as a whole into an envelope surrounding same on all sides, followed by the e.g. bonding, sealing, welding or embossing of all the edges did not prove satisfactory due to the material which had to be used.

According to the invention one surface of the primary pack is formed by the supporting film and to whose top or bottom surface is fixed in the marginal area the surface structure forming the remainder of the pack. Fixing can e.g. take place by heat sealing, welding, embossing or bonding. If the supporting film has the same surface area as the carrier layer, the remaining pack components are fixed to the top surface of the supporting film. If the supporting film projects over the carrier layer, it may be preferable to provide the fixing to the bottom of the projecting parts of the supporting film.

After tearing open the bag-like primary pack the supporting film remains on the back of the carrier layer, which ensures the desired stabilization of the bandaging material during application.

The fixing of the remaining flat packing material to the supporting film and the production of the detachable connection between the supporting film and carrier layer can take place in one step according to the invention.

The choice of the remaining flat packing material is determined by the particular requirements made on the bandaging material to be packed, so that no generally valid, information can be given. Generally, apart from materials containing impermeable paper, polymers or metals, consideration can e.g. be given to those materials which, on the basis of their structure, can be looked upon as textile fabrics. The material choice for the supporting film and the remaining pack need not be the same, but must be matched to the particular requirements. In conventional manner, the pack can be provided with a tear-open aid, such as e.g. tearing threads, desired breaking lines or the like.

In a particularly preferred embodiment of the invention, the bandaging material contains at least one active substance. It can be a transdermal therapeutic system, in which an individual pack is unavoidable.

BRIEF DESCRIPTION OF THE DRAWINGS

The invention is described in greater detail hereinafter relative to the drawings, wherein it is shown.

DESCRIPTION OF PREFERRED EMBODIMENTS

Figure 1:
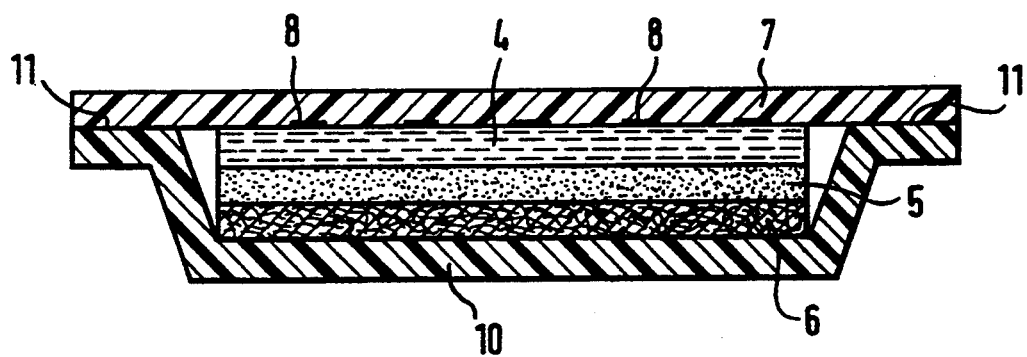
FIG. 1 The diagrammatic cross-section through an embodiment of a bandaging material packed according to the invention.

As shown in FIG. 1, a carrier layer 4 formed from textile material is coated with a pressure sensitive adhesive layer 5, which can contain a pharmacologically active substance and on the skin-facing side has a covering layer 6, which is here made from paper adhesively finished by siliconization. The supporting film 7 projects over the carrier layer 4 on all sides and is made from a multilayer film material more rigid than the carrier layer. It is connected by heat sealing to the carrier layer 4 at points 8 distributed in accordance with a predetermined pattern. During heat sealing a sealing edge 11 is formed with the packing film 10 located below it.

Figure 2:
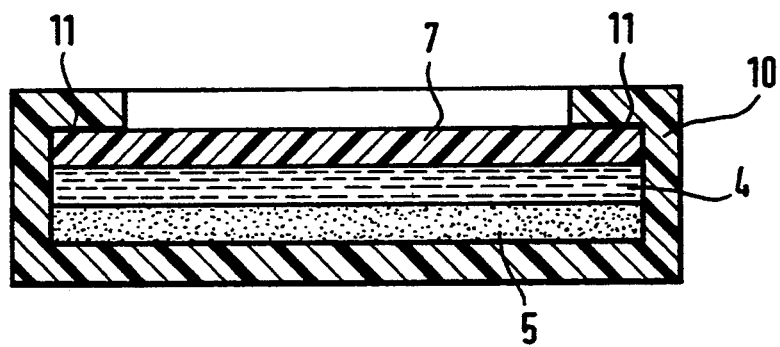
FIG. 2. The diagrammatic cross-section through another embodiment of an inventively packed bandaging material.

FIG. 2 shows another preferred embodiment of the invention in which the supporting film 7 is of the same size as the carrier layer. The packing film 10 surrounds the bandaging material and is bonded at the edges to the top of the supporting film 7. In this case the pressure sensitive adhesive layer 5 has no separate covering layer and instead the packing foil 10 fulfills the protective layer function. The bandaging material can be applied directly after opening the pack.

A preferred embodiment of the inventive bandaging material is described in the following example.

EXAMPLE 1

Production of a packed bandaging material, in which part of the pack functions as a supporting film.

A $15 \times 20$ cm$^2$ bandaging material consisting of a textile carrier layer and an active substance-containing pressure sensitive adhesive layer applied thereto is placed centrally between two heat sealable packing material portions projecting by approximately 1.5 cm on each side. The packing material is chosen in such a way that the portion coming into contact with the carrier layer can assume the function of the supporting film. Edge sealing and the detachable connection of the supporting film to the carrier layer is performed in one or two successive steps. The finished sealing edge bag is then assembled in the usual way.

What is claimed is:

1. A primary packaging unit comprising a surface-stabilized bandaging material, a carrier layer, the carrier layer having a skin-remote surface and a skin-side contact surface, the skin-side contact surface being provided with a pressure sensitive adhesive area and a removable packing layer, and an at least one-layer supporting film detachably bonded to the skin-remote surface of the carrier layer at least pointwise, the supporting film being removable from the applied bandaging material, and forming with the packing layer an exterior envelope part of the packaging for surroundingly enclosing and thereby protecting the bandaging material to provide both support and protection of the bandaging material.

2. Primary packaging for surface-stabilized bandaging material according to claim 1, wherein the carrier layer is made from a layer containing textile material, a polymer material or a metal.

3. Primary packaging according to claim 2, wherein the supporting film is an at least one-layer surface structure of materials containing polymer, paper or metal.

4. Primary packaging according to claim 3, wherein the supporting film is fixed by at least pointwise heat sealing to the carrier layer.

5. Primary packaging according to claim 3, wherein a detachable connection between the carrier layer and the supporting film is produced by an at least partial bonding, by other mechanical or electrostatic forces, or by welding processes.

6. Primary packaging according to claim 1, wherein the packed bandaging material is a transdermal therapeutic system.

7. Primary packaging according to claim 1, wherein the supporting film is of multilayer film material more rigid than the carrier layer.

8. A primary packaging unit comprising a surface-stabilized bandaging material, a carrier layer made from a layer containing textile material, a polymer material or a metal, the carrier layer having a skin-remote surface and a skin-side contact surface, the skin-side contact surface being provided with a pressure sensitive adhesive area and being prior to the use of the bandaging material protected by a removable covering layer; and an at least one-layer supporting film being an at least one-layer surface structure of materials containing polymer, paper or metal and being detachably applied to the skin-remote surface of the carrier layer, the supporting film being removable from the applied bandaging material and forming with the covering layer an exterior envelope part of the packaging for surroundingly enclosing and thereby protecting the bandaging material to provide both support and protection of the bandaging material, and a the carrier layer and the supporting film being bonded at least pointwise, to each other, but detachable from each other, said detachable connection being produced by forming the carrier layer directly on the supporting film by an at least partial bonding, by other mechanical or electrostatic forces, or by a welding process.

9. Primary packaging according to claim 8, wherein the supporting film has a surface area which is at least as large as that of the carrier layer.

10. Primary packaging according to claim 9, wherein the cover layer overlaps, and is marginally fixed to, the supporting film.

11. Primary packaging according to claim 10, wherein the bandaging material contains at least one active substance.

12. Primary packaging according to claim 11, wherein the pressure sensitive adhesive area contains a pharmacologically active substance.

13. Primary packaging according to claim 8, wherein the packed bandaging material is a transdermal therapeutic system.

14. A primary packaging unit comprising a surface-stabilized bandaging material, a carrier layer made from a layer containing textile material, a polymer material or a metal, the carrier layer having a skin-remote surface and a skin-side contact surface, the skin-side contact surface being provided with a pressure sensitive adhesive area and being prior to the use of the bandaging material protected by a removable layer; and an at least one-layer supporting film being an at least one-layer surface structure of materials containing polymer, paper or metal and being detachably applied to the skin-remote surface of the carrier layer, the supporting film being removable from the applied bandaging material and forming with said removable layer an exterior envelope part of the packaging for surroundingly enclosing and thereby protecting the bandaging material to provide both support and protection of the bandaging material, and the carrier layer and the supporting film being bonded at least pointwise, to each other, but detachable from each other, said detachable connection being produced by forming the carrier layer directly on the supporting film by an at least partial bonding, by other mechanical or electrostatic forces, or by a welding process.

15. Primary packaging according to claim 14, wherein the packed bandaging material is a transdermal therapeutic system.

16. Primary packaging according to claim 14, wherein the pressure sensitive adhesive area contains a pharmacologically active substance.

* * * * *